United States Patent [19]
Muntermann

[11] Patent Number: 6,113,595
[45] Date of Patent: Sep. 5, 2000

[54] DEVICE FOR THE LINEAR HIGH-FREQUENCY CATHETER ABLATION OF ENDOMYOCARDIAL TISSUE

[75] Inventor: Axel Muntermann, Wexlar, Germany

[73] Assignee: Bip Acquisition Company Inc., Wilmington, Del.

[21] Appl. No.: 09/091,120

[22] PCT Filed: Apr. 11, 1996

[86] PCT No.: PCT/DE96/00638

§ 371 Date: Jul. 17, 1998

§ 102(e) Date: Jul. 17, 1998

[87] PCT Pub. No.: WO97/21387

PCT Pub. Date: Jun. 19, 1997

[30] Foreign Application Priority Data

Dec. 14, 1995 [DE] Germany ............... 295 19 651 U

[51] Int. Cl.[7] .................................................. A61B 18/18
[52] U.S. Cl. ............................ 606/41; 607/102; 606/34; 600/40
[58] Field of Search .................. 607/89, 92, 96, 607/98–102, 12; 606/34, 37, 40, 41–42, 49–50, 15

[56] References Cited

U.S. PATENT DOCUMENTS

| 5,540,681 | 7/1996 | Strul et al. ............ 606/34 |
| 5,782,824 | 7/1998 | Abela et al. ............ 606/15 |
| 5,797,905 | 8/1998 | Fleishman et al. ............ 606/41 |
| 5,830,209 | 11/1998 | Savage et al. ............ 606/15 |
| 5,837,001 | 11/1998 | Mackey ............ 607/102 |
| 5,885,278 | 3/1999 | Fleishman ............ 606/41 |
| 5,916,214 | 6/1999 | Cosio et al. ............ 606/41 |

FOREIGN PATENT DOCUMENTS

| 0 499 491 A2 | 8/1992 | European Pat. Off. . |
| WO 93/08755 | 5/1993 | WIPO . |

*Primary Examiner*—Linda C. M. Dvorak
*Assistant Examiner*—Roy Gibson
*Attorney, Agent, or Firm*—Darby & Darby

[57] ABSTRACT

The invention concerns a device for the high-frequency catheter ablation of endomyocardial tissue, said device including an ablation catheter and an associated connection to a high-frequency generator or high-frequency ablation apparatus. According to the invention, in order to facilitate catheter ablation and reduce the amount of time and treatment necessary therefor, a catheter arrangement including a plurality of electrodes is provided, wherein a plurality of electrodes can be controlled selectively in order to coagulate preferably endomyocardial tissue.

16 Claims, 2 Drawing Sheets

DEVICE FOR THE LINEAR HIGH-FREQUENCY CATHETER ABLATION OF ENDOMYOCARDIAL TISSUE

FIELD OF THE INVENTION

The invention relates to a device for the high-frequency, particularly radio-frequency and/or microwave, catheter ablation of endomyocardial tissue and to a corresponding ablation catheter.

BACKGROUND OF THE INVENTION

The thermal obliteration of dysrhythmia sites in the surface of the cardiac muscle has proved successful in the treatment of cardiac dysrhythmias, particularly disorders caused by endomyocardial tissue. An ablation catheter was inserted in a controlled manner into the patient's heart and a local coagulation was performed using an essentially point electrode in the surface of the muscle, i.e. in the area of the tissue responsible for the conduction system. In doing so, a coagulation scar down to a depth of 3 to 5 mm was usually generated by a high-frequency generator with frequencies of 300 kHz to 700 kHz. This method does, however, suffer from the drawback that in order to carry out treatment, the ablation catheter must be re-placed several times in the area of the treatment site and that in consequence, the treatment process is time-consuming and labor-intensive.

BACKGROUND OF THE PRIOR ART

WO 93/08755 describes such a catheter for punctiform catheter ablation.

A catheter comprising a plurality of expandable electrodes is known from EP-A-0 499 491 A2, but the use of thermal sensors is not described therein.

The invention is based upon the object of simplifying the catheter ablation of endomyocardial tissue and of reducing the amount of time and treatment necessary for this purpose.

This object is solved in a surprisingly simple manner by a high-frequency catheter ablation device according to claim 1 and by a high-frequency ablation catheter according to for the first time in the surface of the cardiac muscle in a single application.

The linear arrangement of the electrodes also makes it possible to ensure that a zonal rather than just a punctiform interruption of the conduction system is obtained and hence the effect of defects can be more reliably ruled out than was the case with previous treatment techniques. The patient's discomfort is considerably reduced by the shorter treatment period, to which tremendous importance is attached particularly in the case of high-risk patients, rendering the device according to the invention suitable for emergency intensive-care and in-patient treatment.

It has proved advantageous to use high-frequency generators with powers of up to 200 Watt and more or commercially available high-frequency ablation apparatus together with the devices according to the invention. The invention is not, however, restricted to fixed powers of the high-frequency ablation apparatus in use and can be essentially used with any high-frequency ablation apparatus.

If the electrodes are each assigned several thermal sensors with which the operating temperatures of the electrodes can be detected, systematic and metered linear coagulation can be brought about by interaction with a control unit. For this purpose, the operating temperature of the particular electrode is detected and set or regulated by the control unit in terms of its temporal course and absolute level. The device according to the invention can be advantageously operated essentially in three different operating states.

These states are the unregulated, partially regulated and completely regulated operating states. In the unregulated operating state, the radio-frequency energy is applied to the particular electrode of the active catheter portion during predefinable intervals of time, preferably 10 mS respectively.

Very thin and highly elastic catheters can be used for this operating state, because it is possible to dispense with thermal sensors and hence the leads thereto are no longer necessary. The catheters used here are also inexpensive and an ECG unit with adjustable operating parameters that are known per se can be used to monitor them.

Although the temperature of the electrodes is detected in the partially regulated operating state, one temperature sensor is used at a time for more than one electrode. In preferred embodiments of the device according to the invention, one temperature sensor is used at a time either for all the ablation electrodes or for two or three of them at a time. As a result, a catheter which is still very elastic and which exhibits good control characteristics can be obtained.

In the completely regulated operating state, the optimum treatment temperature or optimum energy release can invariably be achieved along the entire active catheter portion by using one temperature sensor at a time for each ablation electrode even under the most critical of conditions, e.g. in the case of difficult coupling to the tissue to be treated.

The measurement of the catheter electrodes, impedance with respect to an indifferent electrode placed on patients can also provide information about the correct position of the active catheter portion relative to the tissue to be treated.

Instead of using a high-frequency generator that emits in the radio-frequency range, it is also part of the invention to use a device which operates in the microwave range.

Temperatures ranging from about 40 to about 80° C., preferably 45, 50, 55 and 60° C., have proved effective in order to perform a local coagulation process. Once this temperature has been reached, the energy supplied by the high-frequency generator or high-frequency ablation apparatus can be reduced or preferably supplied to the next electrode or a load, such as a cooled load resistor.

The high-frequency energy can also be advantageously supplied to the electrodes by being modulated in the form of fixed pulses with varying frequency. It has proved advantageous to increase the temperature initially along a predefinable temporally rising reference curve, whereby it is determined by an actual/target value comparison of the reference curve with the electrode's current temperature value whether energy is to be supplied to the electrode in this cycle or in a later one. As a result, thermally exceeding the target value and accompanying adverse effects on the patient are ruled out with considerable certainty.

By diverting the power which is supplied by the generator, but which is currently not required, to a load, the generator is protected from high fluctuations in load and can make its power available more evenly, regardless of external interference.

Electrodes which were arranged along an uninterrupted line having a length of up to approx. 7 cm in length each separated from one another by isolating zones, preferably at the end of the ablation catheter, proved to be particularly expedient.

The treatment is also supported and its safety promoted if the temperature of a particular electrode and the duration of the energy release to this electrode is depicted on a display means in the partially regulated or completely regulated operating states.

The connection of one or more electrodes to an ECG monitor allows the local action of the heart to be detected and displayed before, during and after treatment, thus providing the doctor in charge with immediate statements on its success.

The number of electrodes needed for ablation, their target temperature, temporal energy supply and/or their respective operating state is expediently adjustable on a control panel.

BRIEF DESCRIPTION OF THE DRAWINGS

The invention will now be described in detail on the basis of preferred embodiments and with reference to the enclosed drawings.

Figure 1:
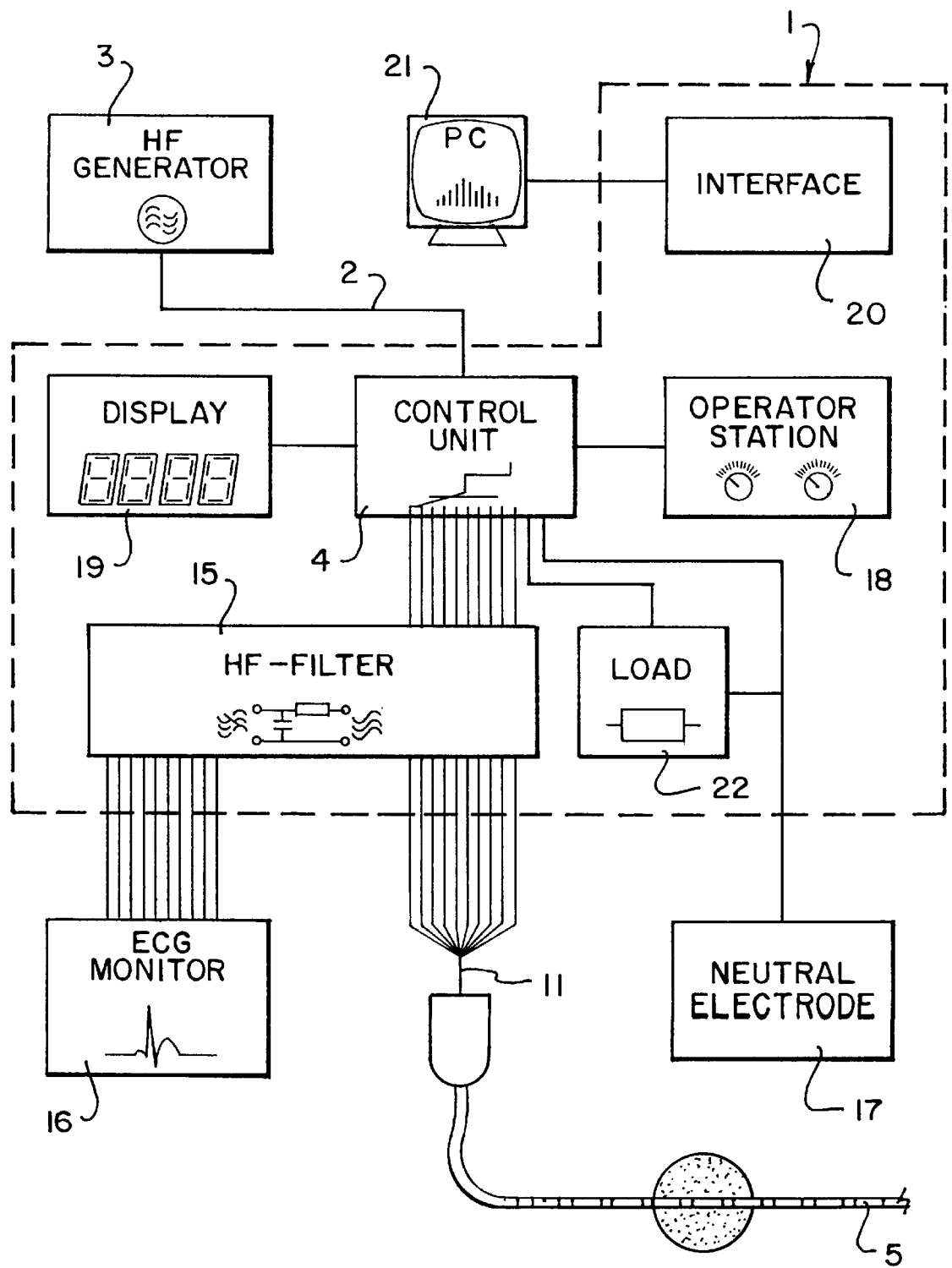
FIG. 1 shows a schematic depiction of the device for linear high-frequency, particularly radio-frequency, catheter ablation.

The following description refers to FIG. 1 in which the device 2 designated as a whole by 1 is shown as a schematic block representation.

The device 1 according to the invention comprises a terminal 2 to a high-frequency generator 3. Instead of the high-frequency generator 3, however, a commercially available high-frequency ablation apparatus 3 or a microwave generator 3 can also be used as an alternative.

In the case of radio-frequency catheter ablation, the frequency range of the devices 3 should extend from about 300 to about 750 kHz or more, and powers of less than 50 W, 120 W, 150 W, 200 W or more can be used. The control unit 4 connects the catheter 5 to the HF generator 3 or high-frequency ablation apparatus 3 in the manner described in more detail as follows.

Figure 2:
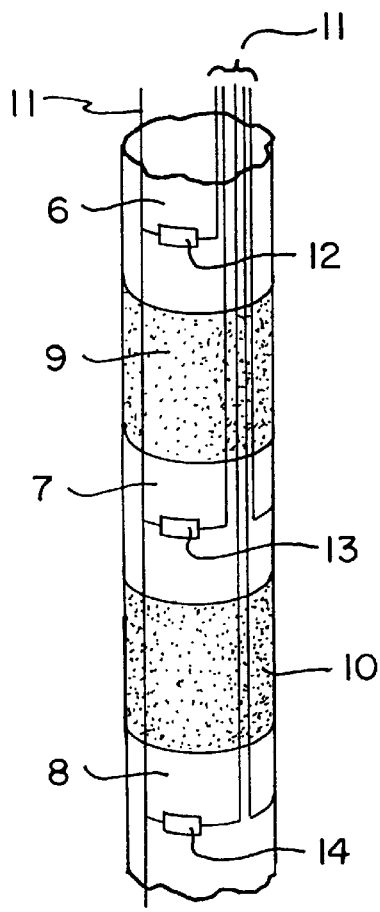
FIG. 2 shows an enlarged depiction of the ablation catheter comprising respective electrodes separated from one another by isolating zones.

As shown in more detail in FIG. 2, the catheter 5 comprises a plurality of selectively controllable electrodes 6, 7 and 8 which are electrically isolated from one another by isolating zones 9 and 10, but which are held in a mechanically flexible manner. In the case of catheters 1 as regards the completely regulated operating state, thermal sensors 12, 13 and 14 assigned to the electrodes 6, 7 and 8 respectively, as well as the electrodes 6, 7 and 8 are electrically connected to the control unit 4 via lines 11.

In the case of the catheters (not shown in the Figures) as regards the partially regulated operating state, fewer thermal sensors 12, 13 and 14 than electrodes 6, 7 and 8 are present at a time. Particularly preferred embodiments of this type of catheter have just a single thermal sensor or have a thermal sensor 12, 13, 14 respectively for two or three electrodes at a time.

In the case of the catheters (not shown in the Figures) as regards the unregulated operating state, thermal sensors are preferably not provided, although the catheters for the partially regulated and completely regulated modes can also be operated in an unregulated manner.

Depending on the design of the device according to the invention, a HF filter 15 either connects a preferably externally disposed unipolar or bipolar ECG monitor 16 to one of the electrodes 6, 7 or 8, connects the device according to the invention to selected electrodes or connects it to all the electrodes of the catheter 5, in order in this way to permit local statements about cardiac action and hence about the behavior of the conduction system before, between, during and after individual coagulation processes or after treatment. A neutral reference or neutral electrode 17 placed on the patient in an easily conductive manner and also designated as an indifferent electrode defines an electrical reference potential for the device 1 according to the invention.

In a further and alternative embodiment according to the invention, the impedance of the electrodes 6, 7, 8 is detected, displayed and/or stored in a chronologically assigned way in relation to the electrode 17 as a gauge for tissue contact. The doctor in charge is therefore able to record the correct implementation of treatment or to detect, evaluate and optimize treatment sequences performed for practice, e.g. in animal experimentation.

The device 1 also comprises an operator station 18 with which the operating parameters can be set via a keypad and/or level elements or actuators. The current operating temperature and temporal course or duration of the supply of high-frequency energy is indicated on a display means 19 which has one or more numerical display panels or a display screen, preferably assigned to the respective sensors. As an alternative or in addition, corresponding bar charts are displayed on a personal computer 21 connected by an interface 20 to the device 1. By means of suitable programs, the treatment parameters can be stored on a memory medium and retrieved afterward.

The functional sequence of the device 1 according to the invention and a treatment sequence will be depicted by way of example as follows.

The operator station 18 and/or personal computer 21 can be used to input the operating parameters needed for treatment, such as quantity and number of the respectively controlled electrodes, temporal duration of control and/or limit temperature.

With a catheter 5 inserted into the patient's heart, the control unit 4 selectively supplies, in a controlled manner, high-frequency energy to the electrodes 6, 7 and 8 during the treatment sequence. Depending on the device's operating state, the momentary temperature is detected in part, completely or not at all by the thermal sensors 12, 13 and 14, and is optionally supplied to the control unit 4. The thermal sensors may comprise thermistors, thermocaps, thermocouples and/or Peltier elements as well as any other sensors suitable for medical applications.

At a temperature ranging from about 40 to about 80° C., preferably 45, 50, 55 or 60° C., local coagulation scars with a depth of about 3 to 5 mm are produced in the heart, whereby the cardiac function can be monitored on the ECG monitor 16 and alternatively the impedance of a few selected or of all the electrodes 6, 7 and 8 can be displayed and recorded.

During periods in which none of the electrodes 6, 7 and 8 are controlled or in which only selected electrodes are controlled, the HF generator 3 or the commercially available high-frequency ablation apparatus 3 can be connected to a load 22 which preferably comprises a cooled resistor, in order to be able to operate the unit 3 in a stable steady state, thus making it possible to avoid power fluctuations. The value of the load impedance roughly corresponds to the impedance of the tissue to be treated and switching over both to the electrodes 6, 7 and 8 and to the load 22 is preferably performed with power FETs in symmetry with the reference potential of the indifferent electrode.

Figure 3:
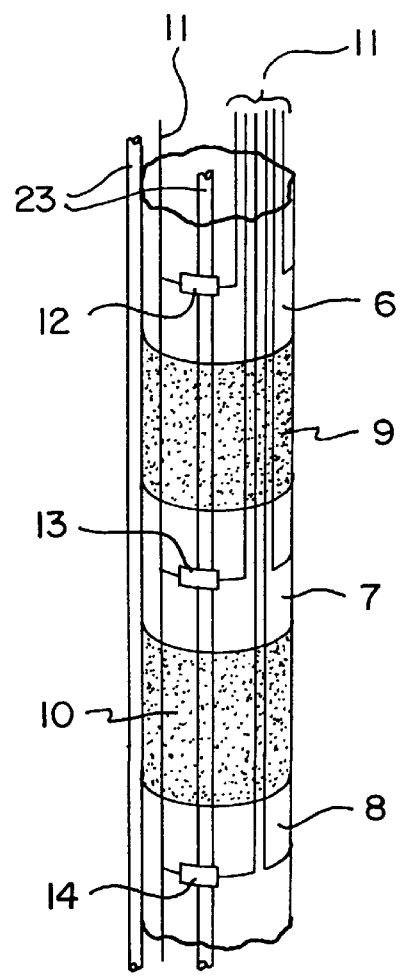
FIG. 3 shows an enlarged depiction of a further embodiment of the ablation catheter comprising optical fibers and respective electrodes separated from one another by isolating zones.

In another embodiment of the invention shown in FIG. 3, the catheter 5 comprises one or more optical fibers 23 each emitting light in a linear manner in the active catheter region. To achieve a defined release of light energy into the tissue, the optical fiber or fibers 23 is or are disposed on the outer or inner periphery of the catheter 5 and permit thermal coagulation by means of light-frequency energy by evaluating the simultaneously detected impedance values. The optical fiber can either have an outlet window extending across the entire active catheter length or various outlet windows of several optical fibers can be arranged similar to the electrodes 6, 7 or 8 so as to enable zonal control. For reliable contact with the tissue to be constantly achieved, a plurality of optical fibers extending parallel to the catheter in the longitudinal direction can be disposed on the catheter's outer or inner periphery.

The progressive success of treatment can be determined using the ECG monitor 16 and by any other monitoring or display equipment known to experts in this field, and can reliably guide the doctor in charge. By using the device according to the invention, existing treatment apparatus, such as HF generators 3, high-frequency ablation equipment 3, ECG monitors 16 or in the case of the latter embodiment existing laser units, can be advantageously used with the catheter 5 according to the invention, and excessively high purchasing costs can be avoided.

The electrodes 6, 7 and/or 8 can also be connected to an apparatus for the bipolar or unipolar electrical stimulation of the cardiac muscle and can in this way contribute, as a result of cardiac stimulation, toward detecting results of the course of treatment.

Furthermore, the invention is not restricted to the advantageous active catheter length of about 7 cm in the case of an electrode size of 4 mm and an isolating zone size of 3 mm. Divergent sizes that are adapted to the particular treatment tasks can easily be implemented by the skilled person or can be set by choosing the number of electrodes 6, 7 or 8 in use. The depicted display and data recording or reproduction equipment likewise merely serves as an example, since in principle any imaging and storing devices can be used.

What is claimed is:

1. A high-frequency ablation catheter for linear endomyocardial catheter ablation, comprising a plurality of electrodes separated from one another by isolating zones, said electrodes being selectively controllable to coagulate tissue; one or more thermal sensors assigned to said electrodes in a selected manner such that the operating temperature of one or more of the electrodes can be detected; and a control unit programmed to operate in one of a plurality of operating states based on the selected assignment of thermal sensors to control delivery of ablation energy to the respective electrodes.

2. A high-frequency ablation catheter according to claim 1, further comprising a connection from one or more of the electrodes to an ECG monitor.

3. A high-frequency ablation catheter according to claim 1, further comprising an optical fiber operative to emit light energy.

4. A device for the high-frequency catheter ablation of endomyocardial tissue, said device comprising an ablation catheter according to claim 1 and one of an associated terminal to a high-frequency generator and a high-frequency ablation apparatus.

5. A device according to claim 4, wherein to perform a local coagulation process, said electrodes each reach a predefinable final temperature ranging between 40 and 80° C.

6. A device according to claim 5, wherein the final temperature is preferably between 45 and 60° C.

7. A device according to claim 4, wherein energy is cyclically or statistically supplied to said electrodes and the energy from said high-frequency generator or high-frequency ablation apparatus is, upon reaching a desired temperature at one of the electrodes, reduced by said control unit or is preferably supplied to another one of the electrodes.

8. A device according to claim 4, wherein energy in the form of electromagnetic pulses having a fixed or variable length or fixed or variable rate of repetition is supplied to said electrodes.

9. A device according to claim 1, wherein the power supplied by said high-frequency generator or high-frequency ablation apparatus, but not presently required is diverted to a load, particularly to one or more resistors which are each cooled.

10. A device according to claim 1, wherein said electrodes are disposed along an uninterrupted line having a length of up to about 7 cm, each separated from one another by isolating zones, preferably at the end of said ablation catheter.

11. A device according to claim 1, wherein said electrodes are each separated from one another by isolating zones at the end of said ablation catheter.

12. A device according to claim 1, wherein the temperature of a particular electrode and the duration of energy release to this electrode can be represented on at least one display means.

13. A device according to claim 1, wherein the local cardiac action before, between, during and after treatment can be detected and displayed by means of a connection from one or more electrodes to an ECG monitor.

14. A device according to claim 1, wherein the number of said electrodes necessary for ablation, their target temperature or temporal energy supply or operating state can be set on an operating panel.

15. A high-frequency ablation catheter, comprising a plurality of electrodes separated from one another by isolating zones, said electrodes being selectively controllable to coagulate tissue; one or more thermal sensors assigned to said electrodes in a selected manner such that the operating temperature of one or more of the electrodes can be detected; and a control unit programmed to deliver ablation energy to the respective electrodes, wherein the ablation energy is diverted to a load when not required by one of the electrodes.

16. A method of performing an ablation procedure with a catheter having a plurality of electrodes separated from one another by isolating zones, the method comprising the steps of:

sequentially delivering ablation energy to the electrodes;

monitoring one or more conditions at one or more of the electrodes; and diverting the ablation energy to a load when one or more of the monitored conditions exceeds a preselected threshold.

* * * * *